United States Patent [19]

Buck

[11] 4,092,114

[45] May 30, 1978

[54] INDIRECT LATEX TEST FOR DETERMINATION OF IMMUNOGLOBULINS

[75] Inventor: Francis Fremonte Buck, Suffern, N.Y.

[73] Assignee: Fisher Scientific Company, Pittsburgh, Pa.

[21] Appl. No.: 734,216

[22] Filed: Oct. 20, 1976

[51] Int. Cl.² ............................................. G01N 33/16
[52] U.S. Cl. .................................. 23/230 B; 424/12; 252/408
[58] Field of Search ..................... 424/12; 23/230 B; 252/408

[56] References Cited

U.S. PATENT DOCUMENTS

| 3,565,987 | 2/1971 | Schuurs | 424/12 |
| 3,857,931 | 12/1974 | Hager | 424/12 |
| 4,003,988 | 1/1977 | Hoff | 252/408 X |

OTHER PUBLICATIONS

A. White et al., "Principles of Biochemistry," 4th Edition, 707–715, McGraw-Hill, New York, 1968.

*Primary Examiner*—Sidney Marantz
*Attorney, Agent, or Firm*—Webb, Burden, Robinson & Webb

[57] ABSTRACT

Indirect test for the qualitative and quantitative determination of immunoglobulins, G, A or M in human body fluid utilizing immuoglobulins (IgG, IgA and IgM) chemically coupled to latex carrier particles as the reagent.

3 Claims, No Drawings

INDIRECT LATEX TEST FOR DETERMINATION OF IMMUNOGLOBULINS

BACKGROUND OF THE INVENTION

Processes for the recovery and isolation of immunoglobulins G, A or M are known, e.g., U.S. Pat. Nos. 3,597,409 and 3,808,189.

It has been established that elevated levels of immunoglobulins M or A in fetal serum is indicative of chronic intrauterine or acute perinatal infections. Deficiencies in levels of IgG, IgA or IgM in older patients may be determined by this method.

At present, the most common commercially available system for determining immunoglobulin levels is the radial immunodiffusion plate. These plates are sold by a number of companies including Hyland, Kallestad, Meloy and Behring under as many different trade names. In this method specific antisera are incorporated into agar or agarose and, as the sample diffuses into the gel, an antigen-antibody precipitin ring is formed. The diameter of the ring is related to the concentration of the antigen. Generally, the times required for development of the rings are 24 to 48 hours which constitutes a major disadvantage particularly in the prenatal field. In contrast to the above, the test system of the present invention provides a result immediately upon completion of the test.

Diagnostic reagents formed by chemically coupling or combining a serologically determinant material to polymeric carrier particles of varying particle size, including latex, particles, are well-known, e.g., U.S. Pat. Nos. 3,882,225; 3,857,931; 3,825,525; 3,639,558; 3,565,987; 3,553,310; 3,407,076; 3,236,732; 3,096,250; Netherlands Pat. No. 7,201,308; and British Pat. No. 1,257,263. Latex particlegamma globulin suspensions have been used in the serologic diagnosis of rheumatoidarthritis, *American Journal of Medicine*, 21: 888–892 (1956).

SUMMARY OF THE INVENTION

The present invention comprises an indirect method for the determination of immunoglobulins A, M or G utilizing a mixture of human immunoglobulins IgA, IgM and IgG, chemically coupled to latex particles. The method is intended for use in the qualitative detection of any one of these immunoglobulins as well as the semi-quantitative determination of the level of any one of these immunoglobulins. Dilutions of the patients serum are mixed with an antiserum specific for the immunoglobulin being assayed. Any such dilution of serum which contains the immunoglobulin in question will neutralize the antiserum thereby inhibiting the agglutination of the immunoglobulin latex by that antiserum. Thus, the absence of agglutination consitutes a positive test result. Utilizing a series of dilutions of a patients serum it is possible to estimate the amount of immunoglobulin in the serum by comparing the agglutination results to those achieved with a reference standard. The specificity of the method of this invention results from the use of specific antisera since the material coupled to the latex is a mixture of antigens.

The latex reagent is coupled with IgG, IgA and IgM, i.e., all three antigens are attached to the latex particle. The specificity for any given immunoglobulin resides in the monospecificity of the antibody used. Each antiserum employed must be reactive with only one of the immunoglobulins. For example, the anti-IgM is monospecific in that it will react only with the IgM on the surface of the latex and not with IgA or IgG. With this latex reagent, then, it is equally possible to set up a test system for IgG or IgA if antiserum monospecific for each immunoglobulin is employed.

Any given immunoglobulin alone could be attached to the latex but the advantage of this invention is that a single indicator reagent can serve for the determination of the three major immunoglobulin classes.

The mixture of immunoglobulins coupled to the latex is prepared from Fraction III-2,1 of human plasma. The processing involves zinc salt precipitation, polyethylene glycol fractionation and caprylic acid precipitation by procedures well known in the art. For example, the preparation of IgM enriched immunoglobulins is described in U.S. Pat. 3,808,189.

The invention is specifically concerned with a indirect method for the qualitative and quantitative determination of immunoglobulins A, M or G (IgA, IgM or IgG) in a body fluid such as adult human serum, cord serum, spinal cord fluid, etc., preferably human serum, which comprises mixing a sample of said body fluid with a antiserum monospecific for immunoglobulins A, M or G; and adding a immunoglobulin latex reagent containing immunoglobulins A, M and G prepared by chemically coupling a mixture of IgA, IgM and IgG to latex particles to said mixture.

The absence of agglutination of the latex particles indicates that IgA, IgM or IgG is present in the sample since the antibody (antisera) is inhibited from reacting with the immunoglobulin latex. If agglutination of the latex occurs, the presence of IgA, IgM or IgG in the sample is excluded since the uninhibited antibody is free to react with the latex reagent. By applying the method serially to different dilutions of the sample a semi-quantitative estimate of the amount of IgA, IgM or IgG present can be made by comparison with a reference standard containing a known amount of IgA, IgM or IgG.

The method of the present invention is suitable for packaging into a diagnostic reagent test kit containing as the essential components thereof the immunoglobulin latex reagent; a prediluted antiserum; applicator straws; and diluent.

A wide-range of carrier particles may be used in the practice of the invention including those disclosed in U.S. Pat. Nos. 3,309,275; 3,551,555; 3,639,558 and 3,857,731. A latex carrier particle size of from about 0.1 to about 2.0 microns is deemed suitable. A most suitable latex carrier particle is the polystyrene particles sold by the Dow Chemical Company in a variety of particle sizes, particularly the 0.79 micron size. Lytron 615, manufactured by the Monsanto Chemical Company, with a particle size of 0.15 to 10.25 microns has also been used.

DETAILED DESCRIPTION OF THE INVENTION

The following will serve to illustrate the invention in more detail.

Preparation of the Reagent

A 100 mg portion of immunoglobulin preparation containing IgA, IgM and IgG in 10 ml of 0.01M phosphate or glycine, 0.15M sodium chloride, pH 8.2 is mixed with 2 ml of 10% latex[Dow Diagnostics (average particle size 0.79 $\mu$)] and 2 ml of a solution of 40 mg/ml of 1-ethyl-3-(3-dimethylaminopropyl) carbodiimide hydrochloride in water. The mixture is heated in a water bath at 5°–55° C for 10 minutes. The reaction mixture is cooled, centrifuged and washed three times with 0.01M phosphate, 0.15M sodium chloride, 0.02% sodium azide, pH 7.0 buffer. The immunoglobulin latex reagent is finally suspended in the phosphate-saline-azide buffer containing 0.02% sodium taurocholate and 0.02% Triton ®x-100.

PERFORMANCE OF THE TEST

In its qualitative aspect, the test is performed on a glass slide which is made up with 3 to 6 depressed ovals built in. In the first step, a drop of a dilution of the sample to be tested (e.g. adult human serum, cord serum, spinal cord fluid, etc.) is placed in each oval along with a drop of antiserum to, for example, human IgM. (The antisera to IgG, IgA or IgM are produced in rabbits or goats by standard procedures known in the art, and are prediluted appropriately for the test.) The antiserum and sample are mixed with an applicator straw and swirled together for about 30 seconds by rotating the slide. In the second step, a drop of the immunoglobulin latex reagent containing IgA, IgM and IgG is added to each mixture of sample and antiserum, mixed with the applicator straw and the whole suspension is swirled by rotating the glass slide for 3 minutes. The absence of agglutination of the latex particles indicates that IgM is present in the sample at the dilution tested, since the antibody is inhibited from reacting with the immunoglobulin latex. If agglutination of the latex occurs, the presence of IgM in the sample is excluded since the uninhibited antibody is free to react with the latex reagent. In its quantitative aspect, by applying this test serially to different dilutions of the sample, a semi-quantitative estimate can be made of the amount of IgM present by comparison with a reference standard containing a known amount of IgM.

Analysis of 25 samples of normal cord serum for IgM levels by the indirect immunoglobulin latex slide test of this invention versus the results of radial immunodiffusion using plates from Kallestad and Behring Laboratories has been performed and such analysis has yielded excellant correlation between the two methods for the level of IgM in cord serum. Similarily good correlations have been achieved between the two different test methods for the levels of IgG and IgA in adult human serum as well as for IgA in cord serum.

We claim:

1. A method for the determination of immunoglobulins A, M or G in a sample of a human body fluid which comprises mixing a sample of said body fluid with antiserum to immunoglobulins A, M or G; and adding an immunoglobulin latex reagent containing immunoglobulins A, M and G chemically coupled to latex particles to said mixture.

2. A method according to claim 1, which comprises applying said method serially to different dilutions of the sample and comparing wih a reference standard.

3. A method according to claim 1 wherein the body fluid is serum.

* * * * *